(12) United States Patent
Lee et al.

(10) Patent No.: US 8,835,154 B2
(45) Date of Patent: Sep. 16, 2014

(54) MICROORGANISM HAVING ENHANCED L-AMINO ACIDS PRODUCTIVITY AND PROCESS FOR PRODUCING L-AMINO ACIDS USING THE SAME

(75) Inventors: Kwang Ho Lee, Daejeon (KR); Keun Chul Lee, Hwaseong-si (KR); Seok Myung Lee, Seoul (KR); Young Bin Hwang, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 13/980,137

(22) PCT Filed: Jan. 18, 2012

(86) PCT No.: PCT/KR2012/000444
§ 371 (c)(1),
(2), (4) Date: Oct. 2, 2013

(87) PCT Pub. No.: WO2012/099396
PCT Pub. Date: Jul. 26, 2012

(65) Prior Publication Data
US 2014/0024087 A1    Jan. 23, 2014

(30) Foreign Application Priority Data
Jan. 18, 2011    (KR) .................. 10-2011-0005136

(51) Int. Cl.
| | | |
|---|---|---|
| C12N 1/20 | (2006.01) | |
| C12N 1/21 | (2006.01) | |
| C12P 1/04 | (2006.01) | |
| C12P 13/22 | (2006.01) | |
| C12P 13/08 | (2006.01) | |
| C12N 9/12 | (2006.01) | |
| C07K 14/245 | (2006.01) | |
| C12N 15/70 | (2006.01) | |

(52) U.S. Cl.
CPC .............. *C12N 15/70* (2013.01); *C12N 9/1205* (2013.01); *C07K 14/245* (2013.01); *C12P 13/227* (2013.01); *C12P 13/08* (2013.01); *C12Y 207/01023* (2013.01)
USPC .......... 435/252.8; 435/106; 435/108; 435/115

(58) Field of Classification Search
None
See application file for complete search history.

(56) References Cited

U.S. PATENT DOCUMENTS

| | | | |
|---|---|---|---|
| 7,229,794 B2 | 6/2007 | Park et al. | |
| 2005/0214911 A1 | 9/2005 | Marchenko et al. | |
| 2008/0009041 A1* | 1/2008 | Mizoguchi et al. | 435/71.1 |
| 2010/0028956 A1 | 2/2010 | Ju et al. | |
| 2011/0111466 A1 | 5/2011 | Ju et al. | |
| 2012/0122163 A1 | 5/2012 | Ju et al. | |

FOREIGN PATENT DOCUMENTS

| | | |
|---|---|---|
| KR | 920008365 | 9/1992 |
| KR | 100576342 | 5/2006 |
| KR | 100792095 | 1/2008 |
| KR | 20100092765 | 8/2010 |
| WO | 2010093182 | 8/2010 |
| WO | 2010101359 | 9/2010 |

OTHER PUBLICATIONS

Fujio et al. Biosci. Biotech. Biochem. 1997, vol. 61, No. 5, p. 840-845, "High Level Expression of XMP Aminase in *Escherichia coli* and Its Application for the Inductrial Production of 5'-Guanylic Acid."
Hara et al. FEMS Microbiol Letter. 2009, vol. 297, p. 217-224, "Glutathione production by efficient ATP-regenerating *Escherichia coli* mutants."
Datsenko et al. PNAS Jun. 6, 2000, vol. 97, No. 12, p. 6640-6645, "One-step inactivation of chromosomal genes in *Escherichia coli* K-12 using PCR products."
Arakawa et al. BMC Biotechnology 2001, vol. 1 No. 7, 8 Pages, "Mutant IoxP vectors for selectable marker recycle and conditional knock-outs."
Takahashi et al. Plant Physiology Sep. 2009, vol. 151, p. 100-113, "Pleiotropic Modulation of Carbon and Nitrogen Metabolism in *Arabidopsis* Plants Overexpressing the NAD kinase2 Gene1W."
Ruiz et al. Phytochemistry 2002, vol. 59, p. 473-478, "Proline metabolism and NAD kinase activity in greenbean plants subjected to cold-shock."
Linder et al. Appl Microbiol Biotechnol. 2010, vol. 87, p. 583-593, "Polyphosphate/ATP-dependent NAD kinase of *Corynebacterium glutamicum*: biochemical properties and impact of ppnK overexpression on lysine production."
Lee et al. Biotechnol Lett 2009, vol. 31, p. 1929-1936, "Thymidine production by overexpressing NAD+ kinase in an *Escherichia coli* recombinant strain."
Li et al. Appl Microbiol Biotechnol 2009, vol. 83, p. 939-947, "Overexpression of NAD kinase in recombinant *Escherichia coli* harboring the phbCAB operon improves polu(3-hydroxybutyrate) production."
Palmeros et al. Gene 2000, vol. 247, p. 255-264, "A family of removable cassettes designed to obtain antibiotic-resistance-free genomic modifications of *Escherichia coli* and other bacteria."
International Search Report for PCT/KR2012/000444, Completed by the Korean Patent Office on Sep. 27, 2012, 5 Pages.
Kawai et al. Eur.J. Biochem. 2001, vol. 268, p. 4359-4365, "Molecular characterization of *Escherichia coli* NAD kinase."
Pollak et al. Biochem. J. 2007, vol. 402, p. 205-218, "The power to reduce: pyridine nucleotides—small moleculaes with a multitude of functions."

(Continued)

*Primary Examiner* — Suzanne M Noakes
*Assistant Examiner* — Jae W Lee
(74) *Attorney, Agent, or Firm* — Brooks Kushman P.C.

(57) ABSTRACT

A microorganism of the genus *Escherichia* having enhanced L-amino acid productivity, wherein the microorganism is transformed to have an enhanced NAD kinase activity and an inactivated activity of an enzyme having an amino acid sequence of SEQ ID NO: 2 encoded by tehB gene and a method for producing L-amino acids using the microorganism of the genus *Escherichia*.

19 Claims, 1 Drawing Sheet

(56) References Cited

OTHER PUBLICATIONS

Kawai et al. Biosci. Biotechnol. Biochem. 2008, vol. 72, No. 4, p. 919-930, "Structure and Function of NAD Kinase and NADP Phosphatase: Key Enzymes That Regulate the Intracellular Balance of NAD(H) and NADP(H)."

Sauer et al. The Journal of Biological Chemistry 2004, vol. 279, p. 6613-6619, "Netabolism and Bioenergetics: The Soluble and Membrane-bound Transhydrogenases UdhA and PntAB Have Divergent Functions in NADPH Metabolism of *Escherichia coli*."

* cited by examiner

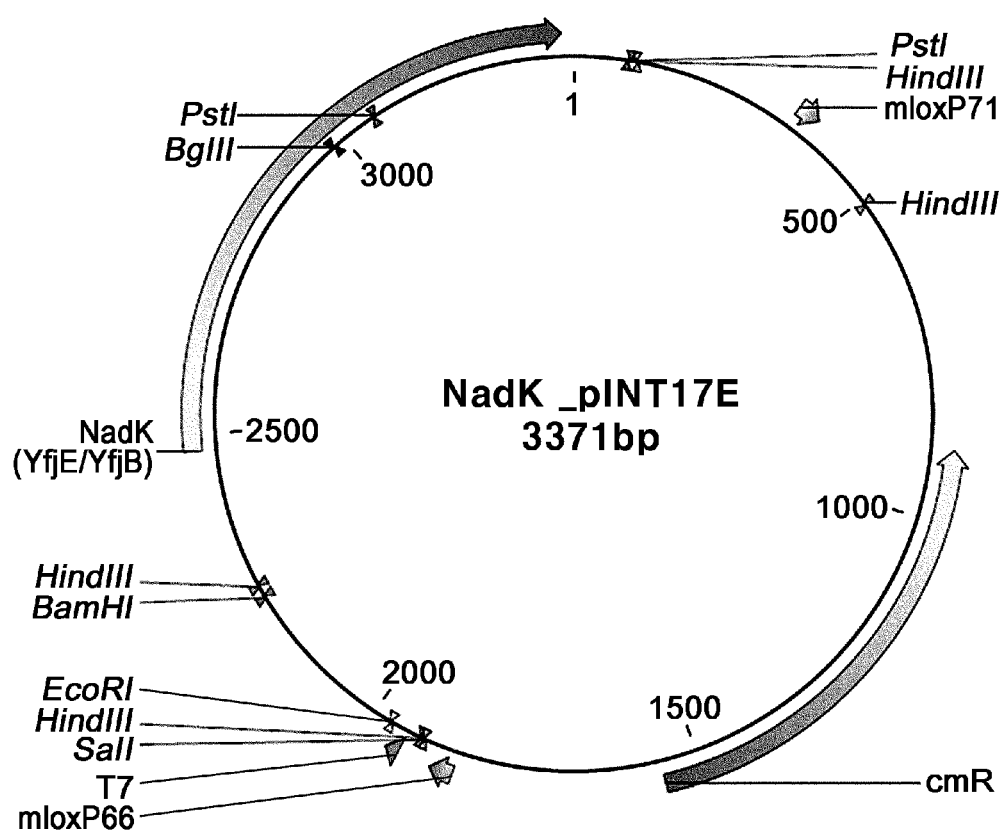

MICROORGANISM HAVING ENHANCED L-AMINO ACIDS PRODUCTIVITY AND PROCESS FOR PRODUCING L-AMINO ACIDS USING THE SAME

CROSS-REFERENCE TO RELATED APPLICATION

This application is the U.S. national phase of PCT Application No. PCT/KR2012/000444 filed on Jan. 18, 2012, which claims priority to Korean Patent Application No. 10-2011-0005136 filed on Jan. 18, 2011, the disclosures of which are incorporated in their entirety by reference herein.

SEQUENCE LISTING

The text file titled Seq_List_10022013.txt of size 24 KB created 30 Sep. 2013, filed therewith, is hereby incorporated by reference.

TECHNICAL FIELD

The present invention relates to a microorganism having an enhanced productivity of useful amino acids through improved cell activity and shortened cell culture time due to increased reducing power, and a method for producing L-amino acids using the same.

BACKGROUND ART

Microorganisms that produce useful products through fermentation are known to require a great amount of energy such as ATP (Adenosine 5'-triphosphate) or reducing power such as NADPH (Nicotinamide Adenine Dinucleotide Phosphate) for enhancement of the biosynthetic pathway thereof.

During the metabolism of microorganisms, the intracellular balance of NADH (nicotinamide adenine dinucleotide) used in catabolic reactions and NADPH (nicotinamide adenine dinucleotide phosphate) used in anabolic reactions are very important. The balance is controlled by phosphorylation of NAD or dephosphorylation of NADP as shown in the following formula.

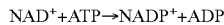

$NAD^+ + ATP \rightarrow NADP^+ + ADP$

$NADP^+ \rightarrow NAD^+ + phosphate$

In *E. coli*, phosphorylation of NAD is known to be catalyzed by an enzyme called NAD kinase (EC 2.7.1.23) encoded by the nadK (or yfjB) gene. NAD kinase utilizes $Mg^{2+}$ as a cofactor of an enzymatic reaction, and is inhibited allosterically by NADPH and NADH. It is known that the Km value for $NAD^+$ is 2000 μM, and that for ATP is 2500 μM (Eur. J. Biochem., (2001) 268: 4359-4365).

Dephosphorylation of NADP has rarely been studied in spite of its central importance in the metabolic pathway. Although an NAD kinase homolog in the archaeon *Methanococcus jannaschii* was shown to have NADP phosphatase activity, genes encoding the enzyme having such activity are not yet identified in eukaryotic and eubacterial sources. In *E. coli*, the product of the cysQ gene showed high NADP and NADPH phosphatase activities, but kinetic studies of the purified enzyme suggested that it is not the true NADP phosphatase of this organism (Biochem J., (2007) 402:205-218, Biosci. Biotechnol. Biochem., (2008) 72:919-930).

NAD kinase activities are found in many microorganisms, and the NAD-binding site and the active site of NAD kinase that are important for catalytic activity show highly conserved amino acid sequences between species. For example, various microorganisms including Gram-positive bacteria show a high level of homology in the tertiary structure prediction of helices 2, 4, and 5 (each of them is indicated by H2, H4, and H5) (Appl Microbiol Biotechnol (2010) 87:583-593).

NADP generated by NAD kinase finally supplies a reducing power, and in particular, NADP+/NADPH required for mass-production of useful products in *E. coli*, is an essential element for anabolic reactions (Biochem J., (2007) 402:205-218). In *E. coli*, NADPH is mainly produced by 1) the oxidative pentose phosphate pathway, 2) NADP-dependent isocitrate dehydrogenase of the TCA cycle (icd gene), and 3) transhydrogenase (pntAB gene) (J Biol. Chem., (2004) 279: 6613-6619).

These reactions produce NADPH using NADP as a substrate, and thus the NADPH level can be increased by increasing the intracellular level of NADP. Therefore, many attempts have been made to increase the intracellular level of NADP for industrial production of various metabolites, for example, 1) NADPH and thymidine production increased by nadK overexpression in *E. coli* (Biotechnol Lett., (2009) 31:19291936), 2) The amount of NADPH and PHB (polyhydroxybutyrate) production increased by nadK overexpression in *E. coli* (Appl Microbiol Biotechnol., (2009) 83:939947), and 3) lysine production increased by ppnK overexpression in *Corynebacterium*, similar to nadK overexpression in *E. coli*. The key point in all of the above cases is to increase the expression of the nadK gene. However, in each of these cases, a phosphate source such as ATP must also be increased in order to increase the reducing power via the increased NADPH level, resulting from the increased NADP level caused by high expression of NAD kinase.

ATP is mainly produced by an electron transport system or substrate level phosphorylation in microorganisms. Produced ATP is decomposed to supply energy to cells, and reproduced through glycolysis or oxidative phosphorylation. Based on this fact, a study of applying a bacterial ATP regeneration system to a production process has been made in order to supply energy during the mass production of useful products (Biosci Biotechnol Biochem., (1997) 61: 840-845).

However, as described above, there are few studies on the method of increasing a phosphate source, which is required for an increase in the reducing power by high expression of NAD kinase and a subsequent increase of biosynthetic products. In addition, an increase in energy supply via high production of ATP has merely been studied in terms of energy supply to cells, and utilization of ATP as a phosphate source has not been studied in the related art.

DISCLOSURE OF INVENTION

Technical Problem

Accordingly, for the development of microorganisms producing high concentration of L-amino acids, the present inventors have made studies on the genes that are involved in various energy and reducing power metabolisms. As a result, they found that a microorganism having enhanced expression of NAD kinase encoded by nadK and the inactivation of an enzyme of an amino acid sequence of SEQ ID NO: 2 encoded by the tehB gene is able to effectively produce a high concentration of L-amino acids, and on this basis, a phosphate source ATP can be effectively increased, thereby completing the present invention.

That is, the present invention relates to a method for increasing production of a desired amino acid by efficiently increasing the reducing power in a microorganism, in which ATP to be reduced during the NADP biosynthetic process is additionally supplied to increase the reducing power of the genus *Escherichia* having L-amino acid productivity.

Therefore, an object of the present invention is to provide a microorganism of the genus *Escherichia* having enhanced L-amino acid productivity, in which the microorganism is transformed to have enhanced NAD kinase activity and an inactivated activity of an enzyme having an amino acid sequence of SEQ ID NO: 2 encoded by the tehB gene, thereby having enhanced reducing power.

Another object of the present invention is to provide a method for producing L-amino acids using the microorganism of the genus *Escherichia*.

Solution to Problem

To achieve the above objects, the present invention provides a microorganism of the genus *Escherichia* having enhanced L-amino acid productivity, in which the microorganism is transformed to have an enhanced NAD kinase activity and an inactivated activity of an enzyme having an amino acid sequence of SEQ ID NO: 2 encoded by the tehB gene.

The present invention also provides a method for producing L-amino acids using the microorganism of the genus *Escherichia*.

Advantageous Effects of Invention

According to the present invention, an supplement of a reducing agent NADPH in intracellular energy metabolism of a microorganism having L-amino acid productivity is created by NADP enhancement, and the subsequent lack of ATP is supplied by the inactivation of an enzyme having an amino acid sequence of SEQ ID NO: 2 encoded by the tehB gene, and thus L-amino acid productivity can be improved by restoring energy metabolism balance and increasing cell activity, and a reduction of cultivation time.

BRIEF DESCRIPTION OF DRAWINGS

FIG. 1 is a diagram showing a vector nadK-pINT17E for increasing the copy number of the nadK gene of *E. coli*.

BEST MODE FOR CARRYING OUT THE INVENTION

The present invention provides a microorganism having enhanced L-amino acid productivity and a method for producing L-amino acids using the same.

The microorganism producing L-amino acids of the present invention comprises any prokaryotic or eukaryotic microorganism, and examples thereof include the microorganism strains belonging to the genus *Escherichia, Erwinia, Serratia, Providencia, Corynebacterium*, and *Brevibacterium*. The microorganism of the present invention is preferably a microorganism belonging to the genus *Escherichia*, and more preferably *E. coli*.

In the present invention, the L-amino acid is preferably L-threonine or L-tryptophan.

In the preferred embodiment of the present invention, the present invention provides a microorganism of the genus *Escherichia* having enhanced L-amino acid productivity, in which the microorganism is transformed to have an enhanced NAD kinase activity and an inactivated activity of an enzyme having an amino acid sequence of SEQ ID NO: 2 encoded by the tehB gene, thereby having enhanced reducing power.

In the present invention, the NAD kinase refers to an enzyme having an activity of converting NAD (nicotinamide adenine dinucleotide) into NADP (nicotinamide adenine dinucleotide phosphate) using a phosphate group derived from ATP or other compounds.

A sequence of the protein having the NAD kinase activity is specifically disclosed as an amino acid sequence of SEQ ID NO: 4, and the nadK gene encoding the NAD kinase is preferably a polynucleotide having a base sequence of SEQ ID NO: 3.

In the present invention, enhancement of the NAD kinase activity of the genus *Escherichia* having L-amino acid productivity can be performed by various methods well known in the art. For example, the method may include a method of inserting an NAD kinase-encoding base sequence itself or a polynucleotide including a foreign expression-regulatory region into a chromosome, a method of increasing the copy number by introducing it into a vector system, or a method of enhancing enzymatic activity by substitution of the gene expression-regulatory region with other regulatory sequence, modification of the entire or a part of the expression-regulatory sequence, or mutation of the gene itself, but is not limited thereto.

More preferably, the present invention can use the method of increasing the copy number by introducing the NAD kinase-encoding base sequence into chromosomal DNA of a strain to enhance the NAD kinase activity of the microorganism belonging to the genus *Escherichia* that has L-amino acid productivity.

It will be appreciated by those skilled in the art that the increased copy number of NAD kinase within the chromosomal DNA shows the same effect as in the increased copy number of NAD kinase by an extrachromosomal vector, or as in the increased expression level by modification of the expression regulatory region of the NAD kinase-encoding nadK gene at the intra- or extra-chromosomal site or mutation of the gene itself. If a vector is used, the genus *Escherichia* having L-amino acid productivity is transformed with the base sequence-introduced recombinant vector, thereby preparing a microorganism of the genus *Escherichia* having enhanced NAD kinase activity.

The vector to be used in the present invention is not particularly limited, and any known expression vector may be used. Preferably, pACYC177, pACYC184, pCL, pECCG117, pUC19, pBR322, or pMW118 vector may be used.

According to one embodiment of the present invention, enhancement of the NAD kinase activity by transformation increases the intracellular NADP and NADPH levels in a strain.

In order to increase ATP production, the present inventors also applied a method of inactivating an activity of an enzyme encoded by the tehB gene.

In the present invention, the tehB gene (NCBI Gene ID: 945979) is known as a gene encoding a tellurite resistance protein or a predicted Sadenosyl-L-methionine-dependent methyltransferase, but its functions still remain unclear.

However, recent studies have reported that a deletion of tehB gene in *E. coli* shows a 150% increase in ATP production, compared to a parental strain, and suggested that this result is attributed to a reduction in ATP required for biosynthesis of S-adenosyl methionine from methionine (FEMS Microbiol Lett., (2009) 297:217-224).

Specifically, a sequence of the predicted S-adenosyl-L-methionine-dependent methyltransferase may be disclosed by an amino acid sequence of SEQ ID NO: 2. In addition, the tehB gene encoding the enzyme is derived from *E. coli*, and preferably a polynucleotide having a base sequence of SEQ ID NO: 1.

The method of inactivating an activity of the enzyme encoded by the tehB gene encompasses all methods of modifying the corresponding gene to prevent production of the enzyme encoded by the gene having the base sequence of SEQ ID NO: 1. The methods may be exemplified by deletion of a part or the entire of the gene by homologous recombination, suppression of enzyme expression by transposon insertion within the corresponding gene, suppression of enzyme expression by insertion of antibiotic resistance genes or the like, but are not limited thereto.

As used herein, the term "transformation" means a method in which a gene is introduced into a host cell to be expressed in the host cell. The transformed genes, if they are in the state of being expressed in the host cell, comprise any of the genes inserted in the chromosome of the host cell or positioned in other parts of the chromosome. In addition, the gene comprises DNA and RNA as a polynucleotide capable of encoding a polypeptide. As long as the gene can be introduced in the host cell and expressed therein, the gene is introduced in any type. For example, the gene can be introduced into the host cell in the type of expression cassette which is polynucleotide expressome comprising by itself whole elements for expressing the gene. The expression cassette comprises a promoter which is operably connected to the gene, transcription termination signal, ribosome binding site and translation termination signal. The expression cassette can be in the type of the expression vector capable of self cloning. The gene also can be introduced into the host cell by itself or in the type of polynucleotide expressome to be operably connected to the sequence necessary for expression in the host cell.

In the preferred embodiment of the present invention, the microorganism transformed by the method can be *E. coli*, and preferably *E. coli* CA03-448(KCCM11167P), CA03-449 (KCCM11168P), or CA04-2001(KCCM11166P).

The present invention also provides a method for producing L-amino acids using the microorganism of the genus *Escherichia*.

In the preferred embodiment of the present invention, the present invention provides the method for producing L-amino acids by culturing the recombinant microorganism of the genus *Escherichia* having an enhanced productivity of L-threonine or L-tryptophan in a medium comprising sucrose or glucose as a main carbon source.

Specifically, the present invention provides a method for producing L-amino acids comprising the steps of inoculating and culturing the recombinant microorganism of the genus *Escherichia* in a culture medium that totally or partially contains sucrose or glucose as a carbon source; and separating the L-amino acids from the culture medium.

The culturing procedures of the present invention may be conducted in suitable media and under culture conditions known in the art. According to the strains used, the culturing procedures can be readily adjusted by those skilled in the art. Examples of the culturing procedures include batch type, continuous type and fed-batch type manners, but are not limited thereto. The media used in the culture method should preferably meet the requirements of a specific strain.

The medium used in the present invention contains sucrose or glucose as a main carbon source. And molasses containing a high concentration of sucrose also may be used as a carbon source and the medium may contain a proper amount of various carbon sources without limitation. Examples of a nitrogen source capable of being used include an organic nitrogen source such as peptone, yeast extract, meat extract, malt extract, corn steep liquor, and soy meal, and an inorganic nitrogen source such as urea, ammonium sulfate, ammonium chloride, ammonium phosphate, ammonium carbonate, and ammonium nitrate, and they can be used either singly or in any combination thereof. To the medium, phosphorus sources such as potassium dihydrogen phosphate, dipotassium hydrogen phosphate or corresponding sodium-containing salts may be added. In addition, the medium may contain metal salts such as magnesium sulfate and ferrous sulfate. Further, the medium may be supplemented with amino acids, vitamins, and appropriate precursors. These media or precursors may be added to cultures by a batch type or continuous type method.

During cultivation, compounds such as ammonium hydroxide, potassium hydroxide, ammonia, phosphoric acid, and sulfuric acid may be properly added so as to adjust the pH of the cultures. Further, during culture, defoaming agents such as fatty acid polyglycol ester may be properly added so as to reduce the formation of foams in cultures. To maintain the cultures in aerobic states, oxygen or oxygen-containing gas may be injected into the cultures. To maintain the cultures in anaerobic and microaerobic states, no gas may be injected or nitrogen, hydrogen, or carbon dioxide gas may be injected into the cultures.

The cultures are maintained at 27 to 37° C., and preferably at 30 to 35° C. The cultivation may be continued until a desired amount of the desired material is obtained, and preferably for 10 to 100 hrs.

The method of collecting and recovering the amino acids produced in the cultivation step of the present invention may be performed by a proper method known in the art, depending on the culturing procedures, for example, batch type, continuous type or fed-batch type, so as to collect the desired amino acid from the culture medium.

MODE FOR THE INVENTION

Hereinafter, the present invention will be described in more detail with reference to Examples. However, these Examples are for illustrative purposes only, and the invention is not intended to be limited by these Examples.

Example 1

Preparation of L-Threonine-Producing Strain Having Inactivation of Enzyme Encoded by *E. coli*-Derived tehB Gene The tehB gene of an L-threonine-producing strain, *E. coli* KCCM10541 (Korean Patent NO. 10-0576342) was deleted by homologous recombination.

The *E. coli* KCCM10541 is a strain derived from an L-threonine-producing strain, *E. coli* KFCC10718 (Korean Patent Publication NO. 10-1992-0008365), and its parental strain, *E. coli* KFCC10718 has a resistance to an L-methionine analogue, a methionine auxotroph phenotype, a resistance to an L-threonine analogue, a leaky isoleucine auxotroph phenotype, a resistance to an L-lysine analogue, and a resistance to α-aminobutyric acid, and is capable of producing L-threonine.

The tehB gene (NCBI Gene ID: 945979) to be deleted is known to encode a predicted S-adenosyl-L-methionine-dependent methyltransferase. When the gene is deleted, ATP used in the production of S-adenosyl methionine is not needed, and thus the tehB gene was selected as a target gene for reduction of energy consumption, and it has a base sequence of SEQ ID NO: 1.

For inactivation, one step inactivation, which is a technique of constructing a mutant using lambda Red recombinase developed by Datsenko K A et al. (Proc Natl Acad Sci USA., (2000) 97:6640 6645), was used.

To confirm the insertion into the gene, a chloramphenicol resistant gene was used as a marker. For removal of the chloramphenicol resistant gene, a Cre/loxP site-specific recombination system was used (BMC Biotechnology (2001) 1:7).

Polymerase chain reaction (hereinbelow, referred to as 'PCR') was performed by using a pMloxCm vector as a template and the following primer 1 and primer 2 having a part of the tehB gene and a part of the sequence of chloramphenicol resistant gene under the conditions: 30 cycles of denaturation at 94° C. for 30 seconds, annealing at 55° C. for 30 seconds and elongation at 72° C. for 1 minute, resulting in the amplification of a gene fragment of approximately 1200 bp.

TABLE 1

| Primer 1 | 5'-GCACACACTCTGAAGTACTGGAAGCGGTGAAAGTGGTTAA ACCGGGTAAAACGCTGGATTAGGTGACACTATAGAACGCG-3' (SEQ ID NO: 6) |
|---|---|
| Primer 2 | 5'-CACCCTCTCCCAGCCTTCGTAATATCGACGTAATTCTCCC TCTTTGAAGGCAAACGGGAATAGTGGATCTGATGGGTACC-3' (SEQ ID NO: 7) |

In addition, the DNA fragment obtained by the PCR amplification was electrophoresed on a 0.8% agarose gel, and then eluted and used as a template for secondary PCR. The secondary PCR was performed by using the eluted primary PCR product as a template and the following primer 3 and primer 4 having 20 bp of a complementary sequence to the 5' and 3' regions of the primary DNA fragment and further having the 5' and 3' regions of the tehB gene under the conditions: 30 cycles of denaturation at 94° C. for 30 seconds, annealing at 55° C. for 30 seconds and elongation at 72° C. for 1 minute, resulting in the amplification of a gene fragment of approximately 1300 bp. The DNA fragment obtained by the above procedure was electrophoresed on a 0.8% agarose gel, and then eluted, and used in recombination.

TABLE 2

| Primer 3 | 5'-GTGACGAAAACTATTTTACTGATAAATATGAATTAACCCG CACACACTCTGAAGTACTG-3' (SEQ ID NO: 8) |
|---|---|
| Primer 4 | 5'-GTCGGTGCGGTGCAGCTCGCCGACGTCTTCATTGTATTTC ACCCTCTCCCAGCCTTCGTA-3' (SEQ ID NO: 9) |

E. coli KCCM 10541 having threonine productivity, which was transformed with a pKD46 plasmid according to the method developed by Datsenko K A et al. (Proc. Natl. Acad. Sci. (2000) 97:6640-6645, GenBank No. AY048746), was prepared as a competent strain, and transformation was performed by introducing the gene fragment of 1300 bp that was obtained by PCR. The obtained strains were selected on the LB medium supplemented with chloramphenicol. A deletion of the tehB gene was confirmed by a PCR product of approximately 2000 bp obtained by PCR using the following primer 5 and primer 6.

TABLE 3

| Primer 5 | 5'-TTTAGGCGCAGGCGTTTTCT-3' (SEQ ID NO: 10) |
|---|---|
| Primer 6 | 5'-TTTTACGTGCCAGCATCGTG-3' (SEQ ID NO: 11) |

After removal of the pKD46 plasmid, the primary recombinant E. coli strain having chloramphenicol resistance was introduced with a pJW168 plasmid so as to remove the chloramphenicol marker gene from the strain (Gene, (2000) 247, 255-264). PCR was performed using the primers 5 and 6 to obtain a PCR product of 832 bp, indicating that the strain finally obtained had the desired deletion.

Example 2

Construction of Vector for Increasing Copy Number of E. coli nadK Gene in Chromosome The gene nadK was amplified by PCR using the chromosome of E. coli W3110 (GeneBank accession number: AC000091) strain purchased from American Type Culture Collection (ATCC) as a template.

Specifically, PCR was performed using the following primers 7 and 8 under the conditions: 30 cycles of denaturation at 94° C. for 30 seconds, annealing at 55° C. for 30 seconds, and elongation at 72° C. for 1 minute, resulting in the amplification of a gene fragment of 1407 bp (SEQ ID NO: 5).

The amplified sequence contains the coding sequence of nadK as well as 501 bp of the predicted self-promoter region. In addition, the primer 7 has a restriction enzyme recognition site for EcoR I, and the primer 8 has a restriction enzyme recognition site for Xba I.

TABLE 4

| Primer 7 | 5'-CCCGAATTCGCGTCAGCTCAATGCCTTCA-3' (SEQ ID NO: 12) |
|---|---|
| Primer 8 | 5'-GGGTCTAGAGCTGGCGTAAAATTAGAATA-3' (SEQ ID NO: 13) |

The obtained polynucleotide was treated with restriction enzymes, Xba I and EcoR I, and cloned into the Xba I and EcoR I sites of the pINT17E vector, followed by transformation into E. coli BW25113. Then, the cells were spread on LB Cm solid medium (LB+chloramphenicol agar plate). The cloned vectors were obtained from the colonies using standard mini-prep procedures, and designated as nadK_pINT17E. The diagram of the vector is shown in FIG. 1.

Example 3

Preparation of L-Threonine-Producing Strain Having Inactivation of Enzyme Encoded by E. coli-Derived tehB Gene and Enhanced NAD Kinase Activity by Increasing its Copy Number in Chromosome The tehB gene-deleted strain prepared according to the method described in Example 1 and the nadK_pINT17E vector prepared according to the method described in Example 2 were used to increase the copy number of NAD kinase.

First, the pKD46 plasmid was introduced into the tehB gene-deleted strain prepared according to the method described in Example 1, and prepared as a competent strain, and the strain was transformed with the nadK_pINT17E vector. Cultivation was performed at 37° C. for 1~2 days to obtain colonies. PCR was performed using primers 8 and 9 to confirm whether the gene is inserted into the chromosome of the obtained colonies. PCR was performed under the following conditions: 30 cycles of denaturation at 94° C. for 30 seconds, annealing at 55° C. for 45 seconds and elongation at 72° C. for 2 minutes, resulting in the amplification of a gene fragment of approximately 2000 bp.

TABLE 5

| Primer 9 | 5'-TGGTATTCACTCCAGAGCGA-3' (SEQ ID NO: 14) |
|---|---|

After the pKD46 plasmid was removed from the primary recombinant strain having the chloramphenicol resistance, the pJW168 plasmid was introduced to remove the chloramphenicol marker gene from the strain (Gene, (2000) 247, 255-264). PCR was performed using primers 10 and 11 to obtain a PCR product of approximately 1500 bp, indicating that two consecutive copies of the nadK gene are desirably present in the chromosome.

The transformed E. coli was designated as KCCM10541ΔtehBnadK 2copy (CA03-448).

TABLE 6

| Primer 10 | 5'-GCATCAGCACCGCGATAAA-3' (SEQ ID NO: 15) |
|---|---|
| Primer 11 | 5'-CATGTGTTGTCAGTGCAGT-3' (SEQ ID NO: 16) |

Example 4

Preparation of L-Tryptophan-Producing Strain Having Inactivation of Enzyme Encoded by E. coli-Derived tehB Gene and Enhanced NAD Kinase Activity by Increasing its Copy Number in Chromosome A transformed E. coli was prepared in the same manner as in Examples 1 to 3, except for using an L-tryptophan-producing strain, E. coli KCCM 10812.

The parental strain used in this Example, E. coli KCCM 10812P, is a strain derived from the mutant E. coli having L-phenylalanine productivity (KFCC 10066), and characterized in that tryptophan auxotrophy is released, pheA, trpR, mtr, and tnaAB genes are inactivated, and aroG and trpE genes are mutated on chromosome (Korean Patent NO. 10-0792095).

The transformed E. coli was designated as KCCM10812ΔtehBnadK 2copy (CA04-2001).

Comparative Example 1

Preparation of L-Threonine or L-Tryptophan-Producing Strain Having Inactivation of Enzyme Encoded by tehB Gene In order to delete the tehB gene, the threonine-producing strain, E. coli KCCM10541 and the tryptophan-producing strain, E. coli KCCM10812 were used as described in Example 1. One step inactivation, which is a technique of constructing a mutant using lambda Red recombinase developed by Datsenko K A et al. (Proc Natl Acad Sci USA., (2000) 97:6640-6645), and the Cre/loxP site-specific recombination system (BMC Biotechnology. (2001) 1:7) were used.

PCR was performed using primers 5 and 6 to obtain PCR products of 832 bp, indicating that the strains finally obtained had the desired deletion, and the strains were designated as KCCM10541ΔtehB and KCCM10812PΔtehB, respectively.

Comparative Example 2

Preparation of L-Threonine or L-Tryptophan-Producing Strain Having Enhanced NAD Kinase Activity According to the method described in Example 3, the copy number of the nadK gene was increased to two copies on the chromosome of the threonine and tryptophan-producing strains so as to prepare strains having enhanced NAD kinase activity.

The pKD46 plasmid was introduced into the threonine-producing strain, KCCM10541, and the tryptophan-producing strain, KCCM10812, and prepared as competent cells, and the strains were transformed with the nadK_pINT17E vector. Thereafter, cultivation was performed at 37° C. for 1-2 days to obtain colonies. PCR was performed using primers 8 and 9 to confirm whether the gene is inserted into the chromosome of the obtained colonies.

After the pKD46 plasmid was removed from the primary recombinant strain having the chloramphenicol resistance, the pJW168 plasmid was introduced to remove the chloramphenicol marker gene from the strain (Gene, (2000) 247, 255-264). PCR was performed using the primers 10 and 11 to obtain PCR products of approximately 1500 bp, indicating that two consecutive copies of the nadK gene are desirably present in the chromosome. The prepared strains were designated as KCCM10541 nadK 2copy and KCCM10812 nadK 2copy, respectively.

Experimental Example 1

Titration of L-Threonine-Producing Strain Having Enhanced NAD Kinase Activity and Inactivation of Enzyme Encoded by tehB Gene Firstly, to provide the L-threonine-producing strain with sucrose-assimilating ability, a pAcscBAR'-mak vector (Korean Patent Publication NO. 10-2010-0092765) (SEQ ID NO: 21) was constructed as follows:

After construction of pAcscBAR, the mak gene was cloned into pAcscBAR. For construction of pAcscBAR, primers 12 and 13 were used to amplify a polynucleotide of cscB region, where cscK was removed.

TABLE 7

| Primer 12 | 5'-CGCGATATCTAGCATATGCCGGGTACCGCACTAGTTGAG AGTAAACGGCGAAGT-3' (SEQ ID NO: 17) |
|---|---|
| Primer 13 | 5'-ATTCGGCCGGAGCCCTGCAGGTGCACGAGTACATTTGAG CGACTGT-3' (SEQ ID NO: 18) |

PCR was performed under the following conditions: after denaturation at 94° C. for 3 minutes, followed by 25 cycles of denaturation at 94° C. for 30 seconds, annealing at 56° C. for 30 seconds, and elongation at 72° C. for 1 minute and 30 seconds, and then elongation at 72° C. for 7 minutes, resulting in the amplification of a polynucleotide of 1521 bp. The obtained polynucleotide and pAcscBAR were treated with restriction enzymes, EcoRV and EagI, respectively, and cloned and transformed into *E. coli* DH5α. Colonies containing pAcscBAR were selected by PCR using the colonies grown on LB media, and plasmids were obtained using standard plasmid mini-prep procedures. No mutation was confirmed by sequence analysis of cscBAR linked at XbaI and EagI sites of the obtained pAcscBAR plasmid.

Primers 14 and 15, and the chromosome of *E. coli* W3110 as a template were used to amplify a polynucleotide containing the mak gene, and cloned into the restriction enzyme sites, PstI and EagI of pAcscBAR, so as to construct the pAcscBAR'-mak vector.

TABLE 8

| Primer 14 | 5'-CACTGCAGTGGGGTAAATGCCATCG-3' (SEQ ID NO: 19) |
| Primer 15 | 5'-AACGGCCGTCTCGGTGCTCATTACT-3' (SEQ ID NO: 20) |

PCR was performed under the following conditions: after denaturation at 94° C. for 3 minutes, followed by 25 cycles of denaturation at 94° C. for 30 seconds, annealing at 56° C. for 30 seconds, and elongation at 72° C. for 1 minute and 30 seconds, and then elongation at 72° C. for 7 minutes, resulting in the amplification of a polynucleotide of 1388 bp. The obtained polynucleotide and pAcscBAR were treated with restriction enzymes, PstI and EagI, respectively, and cloned and transformed into *E. coli* DH5α. Colonies containing pAcscBAR'-mak were selected by PCR using the colonies grown on LB media, and plasmids were obtained using standard plasmid mini-prep procedures. No mutation was confirmed by sequence analysis of cscBAR-mak linked at XbaI and EagI sites of the obtained pAcscBAR'-mak plasmid.

The constructed pAcscBAR'-mak was introduced into the recombinant *E. coli* KCCM10541ΔtehB nadK 2copy strain of Example 3, the parental strain *E. coli* KCCM10541, and the tehB gene-deleted KCCM10541 strain (designated as KCCM10541ΔtehB) and the KCCM10541 strain having increased copy number of nadK gene (designated as KCCM10541 nadK 2copy) prepared in Comparative Examples 1 and 2, respectively, and then titration was performed.

Each of the strains having different genetic traits was cultured on LB solid media in a 33° C. incubator overnight. Thereafter, 1 platinum loop thereof was inoculated in 25 ml of titer medium containing sucrose as shown in the following Table 9, and cultured in the incubator at 33° C. and 200 rpm for 48 hours. The results are shown in Table 10. All results were represented by mean value obtained from three flasks.

TABLE 9

| Composition | Concentration (per liter) |
|---|---|
| Sucrose | 70 g |
| KH$_2$PO$_4$ | 2 g |
| (NH$_4$)$_2$SO$_4$ | 25 g |
| MgSO$_4$7H$_2$O | 1 g |
| FeSO$_4$7H$_2$O | 5 mg |
| MnSO$_4$4H$_2$O | 5 mg |
| L-methionine | 0.15 g |
| Yeast extract | 2 g |
| Calcium carbonate | 30 g |
| pH | 6.8 |

TABLE 10

| strain | OD | Sugar consumption (g/L)* | L-threonine (g/L)** |
|---|---|---|---|
| KCCM10541/pAcscBAR-mak | 16.2 | 34.7 | 31.8 |
| KCCM10541 tehB/pAcscBAR-mak | 15.2 | 35.7 | 32.2 |
| KCCM10541 nadK 2 copy/pAcscBAR-mak | 16.4 | 36.6 | 32.9 |
| KCCM10541 tehBnadK 2copy/pAcscBAR-mak | 14.9 | 37.4 | 34.7 |

*24-hr measured value
**48-hr measured value

As shown in Table 10, when only the tehB gene was deleted, sucrose assimilation ability was similar to that of the parental strain. However, when the NAD kinase activity was enhanced, sucrose assimilation ability was increased to approximately 2 g, compared to the parental strain.

Further, when the tehB gene was deleted, the cell density was reduced to approximately 6%, compared to the parental strain, but its threonine productivity was similar to that of the parental strain. However, when the two mutations were introduced at the same time, the cell density was reduced to approximately 8%, sucrose assimilation ability was increased to approximately 8%, and the threonine productivity was also increased to 9%, compared to the parental strain.

Furthermore, the recombinant *E. coli* KCCM10541ΔtehB nadK 2copy strain of Example 3, the parental strain *E. coli* KCCM10541, and the KCCM10541ΔtehB strain and the KCCM10541 nadK 2copy strain prepared in Comparative Examples 1 and 2 were tested by titration using glucose as a carbon source. Each of the strains having different genetic traits was cultured on LB solid media in a 33° C. incubator overnight. Thereafter, 1 platinum loop thereof was inoculated in 25 ml of titer medium containing glucose as shown in the following Table 11, and cultured in the incubator at 33° C. and 200 rpm for 48 hours. The results are shown in Table 12. All results were represented by mean value obtained from three flasks.

TABLE 11

| Composition | Concentration (per liter) |
|---|---|
| Glucose | 70 g |
| KH$_2$PO$_4$ | 1 g |
| (NH$_4$)$_2$SO$_4$ | 28 g |
| MgSO$_4$7H$_2$O | 0.5 g |
| FeSO$_4$7H$_2$O | 5 mg |
| MnSO$_4$4H$_2$O | 5 mg |
| Yeast extract | 2 g |
| L-methionine | 0.15 g |
| Calcium carbonate | 30 g |
| pH | 6.8 |

TABLE 12

| strain | OD | Sugar consumption (g/L)* | L-threonine (g/L)** |
|---|---|---|---|
| KCCM10541 | 14.0 | 26.7 | 27.6 |
| KCCM10541 tehB | 13.2 | 26.9 | 28.7 |
| KCCM10541 nadK 2 copy | 13.8 | 28.9 | 28.4 |
| KCCM10541 tehBnadK 2copy | 12.5 | 30.3 | 30.1 |

*24-hr measured value
**48-hr measured value

The strain of KCCM10541 ΔtehB nadK 2copy, the L-threonine producing *E. coli* having deleted tehB gene and enhanced NAD kinase activity with glucose-assimilating ability, was designated as CA03-448, and the strain of KCCM10541 ΔtehBnadK 2copy/pAcscBAR'-mak, the strain of KCCM10541 ΔtehB nadK 2copy provided with sucrose-assimilating ability, was designated as CA03-449. And they were deposited in the international depository authority, Korean Culture Center of Microorganisms, which is the Subsidiary Culture Collection of the Korean Federation of Culture Collections, (located at 361-221, Hongje-1-dong, Seodaemon-gu, Seoul, Korea) on Jan. 10, 2011, and assigned Deposit (accession) numbers KCCM11167P and KCCM11168P respectively.

Experimental Example 2

Titration of L-Tryptophan-Producing Strain Having Enhanced NAD Kinase Activity and Inactivation of Enzyme Encoded by tehB Gene The recombinant *E. coli* KCCM10812ΔtehB nadK 2copy strain of Example 4, the parental strain *E. coli* KCCM10812, and the KCCM10812ΔtehB strain and the KCCM10812 nadK 2copy strain prepared in Comparative Examples 1 and 2 were tested by titration using glucose as a carbon source.

For the titration, 1 platinum loop of the strain was inoculated, and cultured on LB solid media overnight. Thereafter, 1 platinum loop thereof was inoculated in 25 ml of flask titer medium having the composition of the following Table 13, and then cultured at 37° C. and 200 rpm for 48 hours. The results are shown in Table 14. All results were represented by mean value obtained from three flasks.

TABLE 13

| Composition | Concentration (per liter) |
| --- | --- |
| Glucose | 60 g |
| K$_2$HPO$_4$ | 1 g |
| (NH$_4$)$_2$SO$_4$ | 10 g |
| NaCl | 1 g |
| MgSO$_4$7H$_2$O | 1 g |
| Sodium citrate | 5 g |
| Yeast extract | 2 g |
| Calcium carbonate | 40 g |
| Sodium citrate | 5 g |
| Phenylalanine | 0.15 g |

TABLE 13-continued

| Composition | Concentration (per liter) |
| --- | --- |
| Tyrosine | 0.1 g |
| pH | 6.8 |

TABLE 14

| strain | OD | Sugar consumption (g/L)* | L-tryptophan (g/L)** |
| --- | --- | --- | --- |
| KCCM10812P | 13.0 | 54.8 | 6.8 |
| KCCM10812P tehB | 14.5 | 55.0 | 7.0 |
| KCCM10812P nadK 2 copy | 13.3 | 57.6 | 6.9 |
| KCCM10812P tehBnadK 2copy | 14.2 | 57.3 | 7.7 |

*33-hr measured value
**48-hr measured value

As shown in Table 14, when the tehB gene was deleted, the cell density was increased to approximately 10%, compared to the parental strain. When the NAD kinase activity was enhanced, glucose assimilation ability was improved, but there was no difference in the tryptophan productivity, compared to the parental strain.

However, when the two mutations were introduced at the same time, the cell density was increased, glucose assimilation ability was also improved, and the tryptophan productivity was increased to approximately 14%.

The strain of KCCM10812P ΔtehB nadK 2copy, the L-tryptophan producing *E. coli* having deleted tehB gene and enhanced NAD kinase activity, was designated as CA04-2001, and it was deposited in the international depository authority, Korean Culture Center of Microorganisms, which is the Subsidiary Culture Collection of the Korean Federation of Culture Collections, (located at 361-221, Hongje-1-dong, Seodaemon-gu, Seoul, Korea) on Jan. 10, 2011, and assigned accession number KCCM11166P.

It will be apparent to those skilled in the art that various modifications and changes may be made without departing from the scope and spirit of the invention. Therefore, it should be understood that the above embodiment is not limitative, but illustrative in all aspects. The scope of the invention is defined by the appended claims rather than by the description preceding them, and therefore all changes and modifications that fall within the metes and bounds of the claims, or equivalents of such metes and bounds, are therefore intended to be embraced by the claims.

The invention claimed is:

1. A microorganism of the genus *Escherichia* having enhanced L-amino acid productivity, wherein the microorganism is transformed to have an enhanced NAD kinase activity and an inactivated activity of an enzyme having an amino acid sequence of SEQ ID NO: 2 encoded by tehB gene.

2. The microorganism according to claim 1, wherein the NAD kinase is a protein having an amino acid sequence of SEQ ID NO: 4.

3. The microorganism according to claim 1, wherein the NAD kinase activity is enhanced by one or more methods of increasing the copy number by chromosomal insertion or vector introduction, substitution or modification of the expression-regulatory region, and gene mutation.

4. The microorganism according to claim 1, wherein the inactivation is performed by one or more methods of deletion of a part or the entire of the gene by homologous recombination, suppression of enzyme expression by transposon insertion within the corresponding gene, and suppression of enzyme expression by insertion of antibiotic resistance genes.

5. The microorganism according to claim 1, wherein the microorganism of the genus *Escherichia* is *E. coli*.

6. The microorganism according to claim 1, wherein the L-amino acid is L-threonine or L-tryptophan.

7. The microorganism according to claim 6, wherein the microorganism of the genus *Escherichia* is provided with sucrose assimilation ability.

8. The microorganism according to claim 1, wherein the microorganism of the genus *Escherichia* is an L-threonine-producing *E. coli*, CA03-448 having Deposit No. KCCM11167P or CA03-449 having Deposit No. KCCM11168P.

9. The microorganism according to claim 1, wherein the microorganism of the genus *Escherichia* is an L-tryptophan-producing *E. coli*, CA04-2001 having Deposit No. KCCM11166P.

10. A method for producing L-amino acids, comprising the steps of inoculating and culturing the microorganism of the genus *Escherichia* of claim 1, in a culture medium that totally or partially contains sucrose or glucose as a carbon source; and separating the L-amino acid from the culture medium.

11. The method according to claim 10, wherein the L-amino acid is L-threonine or L-tryptophan.

12. A method for producing L-amino acids, comprising the steps of inoculating and culturing the microorganism of the genus *Escherichia* of claim 2, in a culture medium that totally or partially contains sucrose or glucose as a carbon source; and separating the L-amino acid from the culture medium.

13. A method for producing L-amino acids, comprising the steps of inoculating and culturing the microorganism of the genus *Escherichia* of claim 3, in a culture medium that totally or partially contains sucrose or glucose as a carbon source; and separating the L-amino acid from the culture medium.

14. A method for producing L-amino acids, comprising the steps of inoculating and culturing the microorganism of the genus *Escherichia* of claim 4, in a culture medium that totally or partially contains sucrose or glucose as a carbon source; and separating the L-amino acid from the culture medium.

15. A method for producing L-amino acids, comprising the steps of inoculating and culturing the microorganism of the genus *Escherichia* of claim 5, in a culture medium that totally or partially contains sucrose or glucose as a carbon source; and separating the L-amino acid from the culture medium.

16. A method for producing L-amino acids, comprising the steps of inoculating and culturing the microorganism of the genus *Escherichia* of claim 6, in a culture medium that totally or partially contains sucrose or glucose as a carbon source; and separating the L-amino acid from the culture medium.

17. A method for producing L-amino acids, comprising the steps of inoculating and culturing the microorganism of the genus *Escherichia* of claim 7, in a culture medium that totally or partially contains sucrose or glucose as a carbon source; and separating the L-amino acid from the culture medium.

18. A method for producing L-amino acids, comprising the steps of inoculating and culturing the microorganism of the genus *Escherichia* of claim 8 in a culture medium that totally or partially contains sucrose or glucose as a carbon source; and separating the L-amino acid from the culture medium.

19. A method for producing L-amino acids, comprising the steps of inoculating and culturing the microorganism of the genus *Escherichia* of claim 9, in a culture medium that totally or partially contains sucrose or glucose as a carbon source; and separating the L-amino acid from the culture medium.

* * * * *

SEQUENCE LISTING

<160> NUMBER OF SEQ ID NOS: 21

<210> SEQ ID NO 1
<211> LENGTH: 594
<212> TYPE: DNA
<213> ORGANISM: Escherichia coli

<400> SEQUENCE: 1

```
atgatcattc gtgacgaaaa ctattttact gataaatatg aattaacccg cacacactct      60
gaagtactgg aagcggtgaa agtggttaaa ccgggtaaaa cgctggatct gggctgtggc     120
aatggtcgta acagtcttta cctggcagcc aatggttatg atgttgacgc atgggataaa     180
aatgccatga gtatcgccaa cgtcgagcgc attaaatcca ttgaaaatct ggataattta     240
cacacccgag tcgttgatct gaataacctc acatttgata gacagtacga ttttattctt     300
```

```
tcgactgtgg tgctgatgtt ccttgaggct aaaaccatcc ccgggttgat tgccaatatg    360
caacgttgca ctaaacctgg tggttacaac ctgattgtgg cggcgatgga taccgctgat    420
tatccatgta ccgtcggctt cccgtttgcc ttcaaagagg gagaattacg tcgatattac    480
gaaggctggg agagggtgaa atacaatgaa gacgtcggcg agctgcaccg caccgacgcc    540
aacggtaatc gtattaaact gcgtttcgcc acgatgctgg cacgtaaaaa atga          594

<210> SEQ ID NO 2
<211> LENGTH: 181
<212> TYPE: PRT
<213> ORGANISM: Artificial Sequence
<220> FEATURE:
<223> OTHER INFORMATION: predicted S-adenosyl-L-methionine-dependent
      methyltrasnferase

<400> SEQUENCE: 2

Arg Thr His Ser Glu Val Leu Glu Ala Val Lys Val Val Lys Pro Gly
1               5                   10                  15

Lys Thr Leu Asp Leu Gly Cys Gly Asn Gly Arg Asn Ser Leu Tyr Leu
            20                  25                  30

Ala Ala Asn Gly Tyr Asp Val Asp Ala Trp Asp Lys Asn Ala Met Ser
        35                  40                  45

Ile Ala Asn Val Glu Arg Ile Lys Ser Ile Glu Asn Leu Asp Asn Leu
    50                  55                  60

His Thr Arg Val Val Asp Leu Asn Asn Leu Thr Phe Asp Arg Gln Tyr
65                  70                  75                  80

Asp Phe Ile Leu Ser Thr Val Val Leu Met Phe Leu Glu Ala Lys Thr
                85                  90                  95

Ile Pro Gly Leu Ile Ala Asn Met Gln Arg Cys Thr Lys Pro Gly Gly
            100                 105                 110

Tyr Asn Leu Ile Val Ala Ala Met Asp Thr Ala Asp Tyr Pro Cys Thr
        115                 120                 125

Val Gly Phe Pro Phe Ala Phe Lys Glu Gly Glu Leu Arg Arg Tyr Tyr
    130                 135                 140

Glu Gly Trp Glu Arg Val Lys Tyr Asn Glu Asp Val Gly Glu Leu His
145                 150                 155                 160

Arg Thr Asp Ala Asn Gly Asn Arg Ile Lys Leu Arg Phe Ala Thr Met
                165                 170                 175

Leu Ala Arg Lys Lys
            180

<210> SEQ ID NO 3
<211> LENGTH: 879
<212> TYPE: DNA
<213> ORGANISM: Artificial Sequence
<220> FEATURE:
<223> OTHER INFORMATION: nadK gene

<400> SEQUENCE: 3
atgaataatc atttcaagtg tattggcatt gtgggacacc cacggcaccc cactgcactg    60
acaacacatg aaatgctcta ccgctggctg tgcacaaaag gttacgaggt catcgttgag    120
caacaaatcg ctcacgaact gcaactgaag aatgtgaaaa ctggcacgct cgcggagatt    180
gggcaactag ctgatctcgc ggtagtcgtt ggtggcgacg gtaatatgct gggcgcggca    240
cgcacactcg cccgttacga tattaaagtt attggaatca accgtggcaa cctgggtttc    300
ctgactgacc ttgaccccga taacgcccag caacagttag ccgatgtgct ggaaggccac    360
```

```
tacatcagcg agaaacgttt tttgctggaa gcgcaagtct gtcagcaaga ttgccagaaa    420
cgcatcagca ccgcgataaa tgaagtggtg cttcatccag gcaaagtggc gcatatgatt    480
gagttcgaag tgtatatcga cgagatcttt gcgttttctc agcgatctga tggactaatt    540
atttcgacgc caacaggctc caccgcctat tccctctctg caggcggtcc tattctgacc    600
ccctctctgg atgcgattac cctggtgccc atgttcccgc atacgttgtc agcacgacca    660
ctggtcataa acagcagcag cacgatccgt ctgcgttttt cgcatcgccg taacgacctg    720
gaaatcagtt gcgacagcca gatagcactg ccgattcagg aaggtgaaga tgtcctgatt    780
cgtcgctgtg attaccatct gaatctgatt catccgaaag attacagtta tttcaacaca    840
ttaagcacca agctcggctg gtcaaaaaaa ttattctaa                          879
```

<210> SEQ ID NO 4
<211> LENGTH: 292
<212> TYPE: PRT
<213> ORGANISM: Artificial Sequence
<220> FEATURE:
<223> OTHER INFORMATION: NAD kinase

<400> SEQUENCE: 4

```
Met Asn Asn His Phe Lys Cys Ile Gly Ile Val Gly His Pro Arg His
1               5                   10                  15

Pro Thr Ala Leu Thr Thr His Glu Met Leu Tyr Arg Trp Leu Cys Thr
            20                  25                  30

Lys Gly Tyr Glu Val Ile Val Glu Gln Gln Ile Ala His Glu Leu Gln
        35                  40                  45

Leu Lys Asn Val Lys Thr Gly Thr Leu Ala Glu Ile Gly Gln Leu Ala
    50                  55                  60

Asp Leu Ala Val Val Gly Gly Asp Gly Asn Met Leu Gly Ala Ala
65                  70                  75                  80

Arg Thr Leu Ala Arg Tyr Asp Ile Lys Val Ile Gly Ile Asn Arg Gly
                85                  90                  95

Asn Leu Gly Phe Leu Thr Asp Leu Asp Pro Asp Asn Ala Gln Gln Gln
            100                 105                 110

Leu Ala Asp Val Leu Glu Gly His Tyr Ile Ser Glu Lys Arg Phe Leu
        115                 120                 125

Leu Glu Ala Gln Val Cys Gln Gln Asp Cys Gln Lys Arg Ile Ser Thr
    130                 135                 140

Ala Ile Asn Glu Val Val Leu His Pro Gly Lys Val Ala His Met Ile
145                 150                 155                 160

Glu Phe Glu Val Tyr Ile Asp Glu Ile Phe Ala Phe Ser Gln Arg Ser
                165                 170                 175

Asp Gly Leu Ile Ile Ser Thr Pro Thr Gly Ser Thr Ala Tyr Ser Leu
            180                 185                 190

Ser Ala Gly Gly Pro Ile Leu Thr Pro Ser Leu Asp Ala Ile Thr Leu
        195                 200                 205

Val Pro Met Phe Pro His Thr Leu Ser Ala Arg Pro Leu Val Ile Asn
    210                 215                 220

Ser Ser Ser Thr Ile Arg Leu Arg Phe Ser His Arg Arg Asn Asp Leu
225                 230                 235                 240

Glu Ile Ser Cys Asp Ser Gln Ile Ala Leu Pro Ile Gln Glu Gly Glu
                245                 250                 255

Asp Val Leu Ile Arg Arg Cys Asp Tyr His Leu Asn Leu Ile His Pro
            260                 265                 270
```

Lys Asp Tyr Ser Tyr Phe Asn Thr Leu Ser Thr Lys Leu Gly Trp Ser
        275                 280                 285

Lys Lys Leu Phe
    290

<210> SEQ ID NO 5
<211> LENGTH: 1407
<212> TYPE: DNA
<213> ORGANISM: Artificial Sequence
<220> FEATURE:
<223> OTHER INFORMATION: PCR product obtained by using primer 7 and
      primer 8

<400> SEQUENCE: 5

```
cccgaattcg cgtcagctca atgccttcaa ccatcgcaga catatccggg ttagctttat      60
cagccacttc cagcgcacga tccaggctat caatcaccgg cagcaattcg ttgatgaatt     120
tctccagcgc gaatttgtgg cttttttcaa tatccagttc agtacgacga cgcaggtttt     180
ccatttcggc ttttacacgc aaaatgccgt cacgttcacg ggtctgggct tcagccagct     240
gagcttcgag attcgcaact ttttcatcgc gcggatccac ctgctcagca gaagcttctg     300
gctcaactgc ctcaatctct tcgtgctgat ccatgataat ttcttccggg gcttgcccct     360
caggcgtttt ctgttcttta ctactcatga atttctccgc gttttttcg cattcatctc     420 gctaacttcg cttattatgg ggatcagttt cagggtttca agggaagcac tcacattgtc     480
atcaatcttc gcaacaagga cctcggaaaa atgaataatc atttcaagtg tattggcatt     540
gtgggacacc cacggcaccc cactgcactg acaacacatg aaatgctcta ccgctggctg     600
tgcacaaaag gttacgaggt catcgttgag caacaaatcg ctcacgaact gcaactgaag     660
aatgtgaaaa ctggcacgct cgcggagatt gggcaactag ctgatctcgc ggtagtcgtt     720
ggtggcgacg gtaatatgct gggcgcggca cgcacactcg cccgttacga tattaaagtt     780
attggaatca accgtggcaa cctgggtttc ctgactgacc ttgaccccga taacgcccag     840
caacagttag ccgatgtgct ggaaggccac tacatcagcg agaaacgttt tttgctggaa     900
gcgcaagtct gtcagcaaga ttgccagaaa cgcatcagca ccgcgataaa tgaagtggtg     960
cttcatccag gcaaagtggc gcatatgatt gagttcgaag tgtatatcga cgagatcttt    1020
gcgttttctc agcgatctga tggactaatt atttcgacgc caacaggctc caccgcctat    1080
tccctctctg caggcggtcc tattctgacc ccctctctgg atgcgattac cctggtgccc    1140
atgttcccgc atacgttgtc agcacgacca ctggtcataa acagcagcag cacgatccgt    1200
ctgcgttttt cgcatcgccg taacgacctg gaaatcagtt gcgacagcca gatagcactg    1260
ccgattcagg aaggtgaaga tgtcctgatt cgtcgctgtg attaccatct gaatctgatt    1320
catccgaaag attacagtta tttcaacaca ttaagcacca gctcggctg gtcaaaaaaa    1380 ttattctaat tttacgccag ctctaga                                       1407
```

<210> SEQ ID NO 6
<211> LENGTH: 80
<212> TYPE: DNA
<213> ORGANISM: Artificial Sequence
<220> FEATURE:
<223> OTHER INFORMATION: primer 1

<400> SEQUENCE: 6

```
gcacacactc tgaagtactg gaagcggtga aagtggttaa accgggtaaa acgctggatt      60
aggtgacact atagaacgcg                                                 80
```

```
<210> SEQ ID NO 7
<211> LENGTH: 80
<212> TYPE: DNA
<213> ORGANISM: Artificial Sequence
<220> FEATURE:
<223> OTHER INFORMATION: primer 2

<400> SEQUENCE: 7
caccctctcc cagccttcgt aatatcgacg taattctccc tctttgaagg caaacgggaa      60
tagtggatct gatgggtacc                                                  80

<210> SEQ ID NO 8
<211> LENGTH: 59
<212> TYPE: DNA
<213> ORGANISM: Artificial Sequence
<220> FEATURE:
<223> OTHER INFORMATION: primer 3

<400> SEQUENCE: 8
gtgacgaaaa ctattttact gataaatatg aattaacccg cacacactct gaagtactg       59

<210> SEQ ID NO 9
<211> LENGTH: 60
<212> TYPE: DNA
<213> ORGANISM: Artificial Sequence
<220> FEATURE:
<223> OTHER INFORMATION: primer 4

<400> SEQUENCE: 9
gtcggtgcgg tgcagctcgc cgacgtcttc attgtatttc accctctccc agccttcgta      60

<210> SEQ ID NO 10
<211> LENGTH: 20
<212> TYPE: DNA
<213> ORGANISM: Artificial Sequence
<220> FEATURE:
<223> OTHER INFORMATION: primer 5

<400> SEQUENCE: 10
tttaggcgca ggcgttttct                                                  20

<210> SEQ ID NO 11
<211> LENGTH: 20
<212> TYPE: DNA
<213> ORGANISM: Artificial Sequence
<220> FEATURE:
<223> OTHER INFORMATION: primer 6

<400> SEQUENCE: 11
ttttacgtgc cagcatcgtg                                                  20

<210> SEQ ID NO 12
<211> LENGTH: 29
<212> TYPE: DNA
<213> ORGANISM: Artificial Sequence
<220> FEATURE:
<223> OTHER INFORMATION: primer 7

<400> SEQUENCE: 12
cccgaattcg cgtcagctca atgccttca                                        29

<210> SEQ ID NO 13
<211> LENGTH: 29
<212> TYPE: DNA
```

```
<213> ORGANISM: Artificial Sequence
<220> FEATURE:
<223> OTHER INFORMATION: primer 8

<400> SEQUENCE: 13
gggtctagag ctggcgtaaa attagaata                                              29

<210> SEQ ID NO 14
<211> LENGTH: 20
<212> TYPE: DNA
<213> ORGANISM: Artificial Sequence
<220> FEATURE:
<223> OTHER INFORMATION: primer 9

<400> SEQUENCE: 14
tggtattcac tccagagcga                                                        20

<210> SEQ ID NO 15
<211> LENGTH: 19
<212> TYPE: DNA
<213> ORGANISM: Artificial Sequence
<220> FEATURE:
<223> OTHER INFORMATION: primer 10

<400> SEQUENCE: 15
gcatcagcac cgcgataaa                                                         19

<210> SEQ ID NO 16
<211> LENGTH: 19
<212> TYPE: DNA
<213> ORGANISM: Artificial Sequence
<220> FEATURE:
<223> OTHER INFORMATION: primer 11

<400> SEQUENCE: 16
catgtgttgt cagtgcagt                                                         19

<210> SEQ ID NO 17
<211> LENGTH: 54
<212> TYPE: DNA
<213> ORGANISM: Artificial Sequence
<220> FEATURE:
<223> OTHER INFORMATION: primer 12

<400> SEQUENCE: 17
cgcgatatct agcatatgcc gggtaccgca ctagttgaga gtaaacggcg aagt                  54

<210> SEQ ID NO 18
<211> LENGTH: 46
<212> TYPE: DNA
<213> ORGANISM: Artificial Sequence
<220> FEATURE:
<223> OTHER INFORMATION: primer 13

<400> SEQUENCE: 18
attcggccgg agccctgcag gtgcacgagt acatttgagc gactgt                          46

<210> SEQ ID NO 19
<211> LENGTH: 25
<212> TYPE: DNA
<213> ORGANISM: Artificial Sequence
<220> FEATURE:
<223> OTHER INFORMATION: primer 14

<400> SEQUENCE: 19
cactgcagtg gggtaaatgc catcg                                                  25
```

<210> SEQ ID NO 20
<211> LENGTH: 25
<212> TYPE: DNA
<213> ORGANISM: Artificial Sequence
<220> FEATURE:
<223> OTHER INFORMATION: primer 15

<400> SEQUENCE: 20
aacggccgtc tcggtgctca ttact                                       25

<210> SEQ ID NO 21
<211> LENGTH: 9129
<212> TYPE: DNA
<213> ORGANISM: Artificial Sequence
<220> FEATURE:
<223> OTHER INFORMATION: pAcscBAR'-mak vector

<400> SEQUENCE: 21

| | | |
|---|---|---|
| tatggcaatg aaagacggtg agctggtgat atgggatagt gttcacccctt gttacaccgt | 60 |
| tttccatgag caaactgaaa cgttttcatc gctctggagt gaataccacg acgatttccg | 120 |
| gcagtttcta cacatatatt cgcaagatgt ggcgtgttac ggtgaaaacc tggcctattt | 180 |
| ccctaaaggg tttattgaga atatgttttt cgtctcagcc aatccctggg tgagtttcac | 240 |
| cagttttgat ttaaacgtgg ccaatatgga caacttcttc gcccccgttt tcaccatggg | 300 |
| caaatattat acgcaaggcg acaaggtgct gatgccgctg gcgattcagg ttcatcatgc | 360 |
| cgtctgtgat ggcttccatg tcggcagaat gcttaatgaa ttacaacagt actgcgatga | 420 |
| gtggcagggc ggggcgtaat tttttttaagg cagttattgg tgcccttaaa cgcctggtgc | 480 |
| tacgcctgaa taagtgataa taagcggatg aatggcagaa attcgaaagc aaattcgacc | 540 |
| cggtcgtcgg ttcagggcag ggtcgttaaa tagccgctta tgtctattgc tggtttaccg | 600 |
| gtttattgac taccggaagc agtgtgaccg tgtgcttctc aaatgcctga ggccagtttg | 660 |
| ctcaggctct ccccgtggag gtaataattg acgatatgat catttattct gcctcccaga | 720 |
| gcctgataaa aacggttagc gcttcgttaa tacagatgta ggtgttccac agggtagcca | 780 |
| gcagcatcct gcgatgcaga tccggaacat aatggtgcag ggcgcttgtt tcggcgtggg | 840 |
| tatggtggca ggccccgtgg ccgggggact gttgggcgct gccggcacct gtcctacgag | 900 |
| ttgcatgata aagaagacag tcataagtgc ggcgacgata gtcatgcccc gcgcccaccg | 960 |
| gaaggagcta ccggacagcg gtgcggactg ttgtaactca gaataagaaa tgaggccgct | 1020 |
| catgcgttac actctcagtc atagtatcgt ggtatcaccg gttggttcca ctctctgttg | 1080 |
| cgggcaactt cagcagcacg tagggggactt ccgcgtttcc agactttacg aaacacggaa | 1140 |
| accgaagacc attcatgttg ttgctcaggt cgcagacgtt ttgcagcagc agtcgcttca | 1200 |
| cgttcgctcg cgtatcggtg attcattctg ctaaccagta aggcaacccc gccagcctag | 1260 |
| ccgggtcctc aacgacagga gcacgatcat gcgcacccgt ggccaggacc caacgctgcc | 1320 |
| cgagatgcgc cgcgtgcggc tgctggagat ggcggacgcg atggatatgt tctgccaagg | 1380 |
| gttggtttgc gcattcacag ttctccgcaa gaattgattg ctccaattc ttggagtggt | 1440 |
| gaatccgtta gcgaggtgcc gccggcttcc attcaggtcg aggtggcccg gctccatgca | 1500 |
| ccgcgacgca acgcggggag gcagacaagg tatagggcgg cgcctacaat ccatgccaac | 1560 |
| ccgttccatg tgctcgccga ggcggcataa atcgccgtga cgatcagcgg tccagtgatc | 1620 |
| gaagttaggc tggtaagagc cgcgagcgat ccttgaagct gtccctgatg gtcgtcatct | 1680 |

```
acctgcctgg acagcatggc ctgcaacgcg ggcatcccga tgccgccgga agcgagaaga   1740
atcataatgg ggaaggccat ccagcctcgc gtcgcgaacg ccagcaagac gtagcccagc   1800
gcgtcggccg tctcggtgct cattacttat tgccggatgc ggcgtgaacg ccttatccgc   1860
cctacgcggt tctggcacat tttgcaggcc tgataagacg cggcaagcgt cgcatcaggc   1920
atcggagcac ttattgccgg atgcggcgtg aacgccttat ccggcctacg gttctggcac   1980
cttttgtagg cctgataaga cgcggcaagc gtcgcatcag gcatgatgcg ccaattgcct   2040 acgttttta ctcttgtggc cataaccacg cagcgccgcg tacgccgctg gaatcaccgt    2100
gcttcgcctt acgcaccggc gtttcacatt cgccgccgaa gacaaattgt ttaatcaact   2160
gcccaaccgt ttgatataaa cggtctacat tgctcatccc gcccccagg acaatcacat    2220 ccggatcgag aatattccg acatgtgcca gcgattttgc cagccgcagc tcgtagcgac    2280
gcaatgccag ttccgctacc ggatcgcttt cttcaaccag gcggataatt tcactgcctt   2340
tcagcgcatg tccgctcaaa cgacgataat ccatcgcgaa tcccgtgccc gaaataaagg   2400
tttcaataca accttgttta ccgcaataac aagggacttc ctcgcgataa cgcagttcgt   2460
cttcgtccat ccacggtagc ggattgtgtc cccactcacc tgccgtgcca ttgccgccga   2520
tatgcgcccg cccattgaat gccacgcccg cgccgcatcc cgtgccgata tcacggcaa    2580 ataccgtctg cgctcccgct gccgcgccat ctactgcttc tgaaaccgcc agacagttag   2640
cgtcatttgc cagccgcact tccgctgca acctcgcgct taagtcttta tcgaatggct    2700
gaccgttgag ccaggttgaa ttggcattct tcaccacacc ggtgtaaggc gaaattgagc   2760
caggaatgcc catacctacc gttccgcgct gccccgtcgc ctgctccgcc atatcaacca   2820
acgtggcgat cgtttcaata gtctgccggt aatcatcacg cggcgtgggc agacgatggc   2880
ggtacaactg ctcccctgca tcgcccagtg caatcacttc agttttggtg ccgcctaaat   2940
cgatacctat acgcacggta ctctccttat ttttttcaat atcaatagcg tagagacgga   3000
caaccggatt ggcaatgcaa ggccgccgac aattcgttat catgcccgct aaatttaacg   3060
acaaggccgt ggaaattatc atgctgtggt tcaaaaattt aatggtttac cgtcttagcc   3120
gcgagatttc gctgcgtgca gaagagatgg aaaaacagct agcctcgatg gcatttaccc   3180
cactgcaggt gcacgagtac atttgagcga ctgtaccaga acatgaatga ggcgtttgga   3240
ttaggcgatt attagcaggg ctaagcattt tactattatt attttccggt tgagggatat   3300
agagctatcg acaacaaccg gaaaagttt acgtctatat tgctgaaggt acaggcgttt    3360
ccataactat ttgctcgcgt ttttactca agaagaaaat gccaaatagc aacatcaggc    3420
agacaatacc cgaaattgcg aagaaaactg tctggtagcc tgcgtggtca agagtatcc    3480 cagtcggcgt tgaaagcagc acaatcccaa gcgaactggc aatttgaaaa ccaatcagaa   3540
agatcgtcga cgacaggcgc ttatcaaagt ttgccacgct gtatttgaag acggatatga   3600
cacaaagtgg aacctcaatg gcatgtaaca acttcactaa tgaaataatc caggggttaa   3660
cgaacagcgc gcaggaaagg atacgcaacg ccataatcac aactccgata agtaatgcat   3720
tttttggccc tacccgattc acaaagaaag gaataatcgc catgcacagc gcttcgagta   3780
ccacctggaa tgagttgaga taaccataca ggcgcgttcc tacatcgtgt gattcgaata   3840
aacctgaata aaagacagga aaagttgtt gatcaaaaat gttatagaaa gaccacgtcc     3900
ccacaataaa tatgacgaaa acccagaagt ttcgatcctt gaaaactgcg ataaaatcct   3960
ctttttttac ccctcccgca tctgccgcta cgcactggtg atccttatct ttaaaacgca   4020
tgttgatcat cataaatata gcgccaaata gcgagaccaa ccagaagttg atatggggac   4080
```

```
tgatactaaa aaatatgccg gcaaagaacg cgccaatagc atagccaaaa gatccccagg   4140
cgcgcgctgt tccatattcg aaatgaaaat ttcgcgccat tttttcggtg aagctatcaa   4200
gcaaaccgca tcccgccaga taccccccagc caaaaaacag cgcccccaga attagaccta   4260
cagaaaaatt gctttgcagt aacgttcat aaacgtaaat cataaacggt ccggtcaaga    4320
ccaggatgaa actcatacac cagatgagcg gtttcttcag accgagttta tcctgaacga   4380
tgccgtagaa catcataaat agaatgctgg taaactggtt gaccgaataa agtgtaccta   4440
attccgtccc tgtcaaccct agatgtcctt tcagccaaat agcgtataac gaccaccaca   4500
gcgaccagga aataaaaaag agaaatgagt aactggatgc aaaacgatag tacgcatttc   4560
tgaatggaat actcagtgcc ataattacct gcctgtcgtt aaaaaattca cgtcctattt   4620
agagataaga gcgacttcgc cgtttacttc tcaactagtg cggtacccgg catatgctag   4680
atatcgactc cctcagttag cagcgttctt tgcattaacg caccaaaagg atcatccccc   4740
acccgaccta taaacccact tgttccgcct aatctggcga ttcccaccgc aacgttagct   4800
ggcgcgccgc caggacaagg cagtaggcgc ccgtctgatt ctggcaagag atctacgacc   4860
gcatccccta aaacccatac tttggctgac attttttcc cttaaattca tctgagttac    4920
gcatagtgat aaacctcttt ttcgcaaaat cgtcatggat ttactaaaac atgcatattc   4980
gatcacaaaa cgtcatagtt aacgttaaca tttgtgatat tcatcgcatt tatgaaagta   5040
agggacttta ttttataaa agttaacgtt aacaattcac caaatttgct taaccaggat    5100
gattaaaatg acgcaatctc gattgcatgc ggcgcaaaac gccctagcaa aacttcatga   5160
gcaccggggt aacactttct atccccattt tcacctcgcg cctcctgccg ggtggatgaa   5220
cgatccaaac ggcctgatct ggtttaacga tcgttatcac gcgttttatc aacatcatcc   5280
gatgagcgaa cactgggggc caatgcactg gggacatgcc accagcgacg atatgatcca   5340
ctggcagcat gagcctattg cgctagcgcc aggagacgat aatgacaaag acgggtgttt   5400
ttcaggtagt gctgtcgatg acaatggtgt cctctcactt atctacaccg gacacgtctg   5460
gctcgatggt gcaggtaatg acgatgcaat tcgcgaagta caatgtctgg ctaccagtcg   5520
ggatggtatt catctcgaga aacagggtgt gatcctcact ccaccagaag gaatcatgca   5580
cttccgcgat cctaaagtgt ggcgtgaagc cgacacatgg tggatggtag tcggggcgaa   5640
agatccaggc aacacggggc agatcctgct ttatcgcggc agttcgttgc gtgaatggac   5700
cttcgatcgc gtactggccc acgctgatgc gggtgaaagc tatatgtggg aatgtccgga   5760 cttttttcagc cttggcgatc agcattatct gatgttttcc ccgcagggaa tgaatgccga   5820
gggatacagt taccgaaatc gctttcaaag tggcgtaata cccggaatgt ggtcgccagg   5880 acgactttt gcacaatccg ggcattttac tgaacttgat aacggcatg acttttatgc    5940 accacaaagc tttttagcga aggatggtcg gcgtattgtt atcggctgga tggatatgtg   6000
ggaatcgtca atgccctcaa aacgtgaagg atgggcaggc tgcatgacgc tggcgcgcga   6060
gctatcagag agcaatggca aacttctaca acgcccggta cacgaagctg agtcgttacg   6120
ccagcagcat caatctgtct ctccccgcac aatcagcaat aaatatgttt tgcaggaaaa   6180
cgcgcaagca gttgagattc agttgcagtg ggcgctgaag aacagtgatg ccgaacatta   6240
cggattacag ctcggcactg gaatgcggct gtatattgat aaccaatctg agcgacttgt   6300
tttgtggcgg tattacccac acgagaattt agacggctac cgtagtattc ccctcccgca   6360
gcgtgacacg ctcgccctaa ggatatttat cgatacatca tccgtggaag tatttattaa   6420
```

```
cgacggggaa gcggtgatga gtagtcgaat ctatccgcag ccagaagaac gggaactgtc    6480
gctttatgcc tcccacggag tggctgtgct gcaacatgga gcactctggc tactgggtta    6540
acataatatc aggtggaaca acggatcaac agcgggcaag ggatccgcgt cactcttccc    6600
ccttcacgac cttcaataat atgcaatgca gcttcccgcc cgataatgtc atgtggaagc    6660
tgaattgtgg tcagcggcgg taaaaacaga tgcccgacgc caaccagatt atcaaagccc    6720
attacggcga catcctgcgg gattcgtacc cccttcgcca gaagaacctg ataagccaca    6780
aaggctgcgc gatcgttacc acatatcaga acatcaaaat ctggttttgcc cggtttgaag    6840 tgggcattga gtaaacttgc gagatcggtg tagtgatcat cacctgttgc catgtgaaat    6900
tgtttcacct cagccagatc tcgttcagca tcacgccagg cctgctcaaa tccctgccga    6960 cgatacccctg ttgccaacgc actttccggt agccagaagc ataacggttg acgatagccc    7020
gccgcgagca aatgctgtgt tgattcatat tgtgcagtgt aatcatcagg gatataactg    7080
ggtaacgctg ggtcatccgc cacacagttc gccaatacaa tattttcacc atacagagac    7140
tcaggcagcg tgatatatcg cagccccatt gtagtataga taatgccatc cggacggtgg    7200
gcaagcagct gacgtgccgc gcgggcagcg tcatcttcag aaaaaatatt gattaaaaaa    7260
ctattccagc cgaactcgct ggcggttttgc tcaatggcaa gcagaatatc aacagagaaa    7320
ggagtggtag ccgtgtcctg cgccagcacg gcgagagtcg acggcttacg tccttgagcg    7380
cgcatcttac gggcggaaag atcaggaaca taattcaggg tctggattgc ctgcaatacg    7440
cggtcacgcg ttgcaggacg cacagattct gcattatgca tcacccggga gactgtcatc    7500
atcgacactc ccgccaggcg tgcgacatcc tttaatgaag ccatacccaa gccgtttgcc    7560
gtaaaacggg cactgtagca gaaacagacg tcactggcga gatccaacgc cctatcacct    7620
gacacagcaa tacaataaaa aataacaata attcccggac aattgtcccc agttccgcct    7680
ctgttctcgc caacgagtct agaaatattt tatctgatta ataagatgat cttcttgaga    7740 tcgtttttggt ctgcgcgtaa tctcttgctc tgaaaacgaa aaaaccgcct tgcagggcgg    7800 ttttttcgaag gttctctgag ctaccaactc tttgaaccga ggtaactggc ttggaggagc    7860
gcagtcacca aaacttgtcc tttcagttta gccttaaccg cgcatgact tcaagactaa    7920 ctcctctaaa tcaattacca gtggctgctg ccagtggtgc ttttgcatgt ctttccgggt    7980
tggactcaag acgatagtta ccggataagg cgcagcggtc ggactgaacg gggggttcgt    8040
gcatacagtc cagcttggag cgaactgcct acccggaact gagtgtcagg cgtggaatga    8100
gacaaacgcg gccataacag cggaatgaca ccggtaaacc gaaaggcagg aacaggagag    8160
cgcacgaggg agccgccagg gggaaacgcc tggtatcttt atagtcctgt cgggtttcgc    8220
caccactgat ttgagcgtca gatttcgtga tgcttgtcag gggggcggag cctatggaaa    8280
aacggctttg ccgcggccct ctcacttccc tgttaagtat cttcctggca tcttccagga    8340
aatctccgcc ccgttcgtaa gccatttccg ctcgccgcag tcgaacgacc gagcgtagcg    8400
agtcagtgag cgaggaagcg gaatatatcc tgtatcacat attctgctga cgcaccggtg    8460 cagcctttt tctcctgcca catgaagcac ttcactgaca ccctcatcag tgccaacata    8520
gtaagccagt atacactccg ctagcgctga tgtccggcgg tgcttttgcc gttacgcacc    8580 acccccgtcag tagctgaaca ggagggacag ctgatagaaa cagaagccac tggagcacct    8640
caaaaacacc atcatacact aaatcagtaa gttggcagca tcacccgacg cactttgcgc    8700
cgaataaata cctgtgacgg aagatcactt cgcagaataa ataaatcctg gtgtccctgt    8760
tgataccggg aagccctggg ccaacttttg gcgaaaatga gacgttgatc ggcacgtaag    8820
```

```
aggttccaac tttcaccata atgaaataag atcactaccg ggcgtatttt ttgagttatc    8880
gagattttca ggagctaagg aagctaaaat ggagaaaaaa atcactggat ataccaccgt    8940
tgatatatcc caatggcatc gtaaagaaca ttttgaggca tttcagtcag ttgctcaatg    9000
tacctataac cagaccgttc agctggatat tacggccttt ttaaagaccg taaagaaaaa    9060
taagcacaag ttttatccgg cctttattca cattcttgcc cgcctgatga atgctcatcc    9120
ggaattccg                                                            9129
```